(12) United States Patent
Hanson et al.

(10) Patent No.: US 11,561,213 B2
(45) Date of Patent: Jan. 24, 2023

(54) SYSTEM AND METHOD FOR MEASURING SMOKE ABSORPTION INTO FOOD PRODUCTS

(71) Applicant: Sugar Creek Packing Co., Washington Court House, OH (US)

(72) Inventors: Robert E. Hanson, Hudson, WI (US); Richard L. McKenzie, Loveland, OH (US)

(73) Assignee: Sugar Creek Packing Co., Washington Court House, OH (US)

( * ) Notice: Subject to any disclaimer, the term of this patent is extended or adjusted under 35 U.S.C. 154(b) by 142 days.

(21) Appl. No.: 17/089,287

(22) Filed: Nov. 4, 2020

(65) Prior Publication Data

US 2021/0048420 A1 Feb. 18, 2021

Related U.S. Application Data

(63) Continuation-in-part of application No. 16/377,840, filed on Apr. 8, 2019, now Pat. No. 11,116,229, and a continuation-in-part of application No. 15/948,513, filed on Apr. 9, 2018, now Pat. No. 10,834,932, application No. 16/377,840, which is a
(Continued)

(51) Int. Cl.
*G01N 33/02* (2006.01)
*A23B 4/052* (2006.01)
*A23L 27/27* (2016.01)

(52) U.S. Cl.
CPC ............ *G01N 33/02* (2013.01); *A23B 4/052* (2013.01); *A23L 27/27* (2016.08)

(58) Field of Classification Search
CPC .......... G01N 33/02; A23B 4/052; A23L 27/27
See application file for complete search history.

(56) References Cited

U.S. PATENT DOCUMENTS 3,943,841 A 3/1976 Huang
4,558,196 A 12/1985 Babasade
(Continued)

FOREIGN PATENT DOCUMENTS

CN 206177874 5/2017

OTHER PUBLICATIONS

PCT, International Search Report and Written Opinion, International Application No. PCT/US2019/026296 (dated Jun. 26, 2019).
(Continued)

*Primary Examiner* — Alvaro E Fortich
(74) *Attorney, Agent, or Firm* — Thompson Hine LLP

(57) ABSTRACT

In an exemplary embodiment, a system for measuring smoke absorption into food products includes a surrogate that reacts to a presence of smoke in air ambient to the surrogate and the food products, the surrogate including an open container of a liquid and a probe in the form of a toroidal conductivity sensor that measures electrical conductivity of the liquid; wherein the electrical conductivity of the liquid increases as smoke is absorbed by the liquid and simultaneously into the food products; and a control that receives a signal from the toroidal conductivity sensor and in response generates a signal and/or a display indicative of the electrical conductivity of the liquid that corresponds to a selected amount of smoke absorption by the food products exposed to the smoke.

24 Claims, 7 Drawing Sheets

Related U.S. Application Data continuation-in-part of application No. 15/948,513, filed on Apr. 9, 2018, now Pat. No. 10,834,932.

(56) References Cited

U.S. PATENT DOCUMENTS

| | | | |
|---|---|---|---|
| 5,459,078 A | 10/1995 | Kline et al. | |
| 7,036,452 B1 | 5/2006 | Tester | |
| 8,080,268 B2 | 12/2011 | Willfer et al. | |
| 9,408,403 B1 | 8/2016 | Joly et al. | |
| 10,834,932 B2 | 11/2020 | Hanson et al. | |
| 2003/0045608 A1 | 3/2003 | Ochiai et al. | |
| 2004/0146610 A1 | 7/2004 | Lee et al. | |
| 2005/0222778 A1 | 10/2005 | Levinson et al. | |
| 2006/0188615 A1 | 8/2006 | Wilfer et al. | |
| 2008/0182035 A1 | 7/2008 | Samuels | |
| 2008/0211518 A1* | 9/2008 | Hancock | G01R 27/02 324/647 |
| 2009/0118175 A1 | 5/2009 | Macina | |
| 2009/0314066 A1 | 12/2009 | Nieuwenhuis et al. | |
| 2010/0170450 A1* | 7/2010 | Bradley | A01K 63/042 119/261 |
| 2012/0093984 A1 | 4/2012 | Haus, Jr. et al. | |
| 2014/0023756 A1 | 1/2014 | Joly et al. | |
| 2014/0210127 A1 | 7/2014 | Sebastian | |
| 2015/0030728 A1 | 1/2015 | Raghavan et al. | |
| 2016/0213014 A9* | 7/2016 | Joly | A23L 27/16 |
| 2016/0317060 A1* | 11/2016 | Connor | G16H 20/60 |
| 2017/0269015 A1* | 9/2017 | Günther | G01N 27/025 |

OTHER PUBLICATIONS

U.S. Non-Final Office Action; U.S. Appl. No. 15/948,513; 18 pages (dated Jan. 27, 2020).

English translation of CN 206177874, 17 pages (published May 17, 2017).

U.S. Notice of Allowance, U.S. Appl. No. 15/948,513, 25 pages (dated Jul. 8, 2020).

U.S. Non-Final Office Action; U.S. Appl. No. 16/377,840; 22 pages (dated Feb. 12, 2021).

* cited by examiner

SYSTEM AND METHOD FOR MEASURING SMOKE ABSORPTION INTO FOOD PRODUCTS

TECHNICAL FIELD

This disclosure relates to food preparation systems and processes, and more particularly, to systems and processes for imparting a smoke flavor to food products.

BACKGROUND

A goal of commercial food preparation systems and processes is to produce a food product that is consistently of high quality in a minimal amount of preparation time. Such systems and processes must produce high quality food products whose taste, texture, and appearance consistently falls within a desired range, and which minimizes rejects. Achieving such consistency in commercial food product preparation is particularly difficult when smoking food products. Smoking is a process in which food is flavored and/or cooked by exposing it to smoke from burning or smoldering material, typically wood. Providing consistency in imparting smoke flavor to food is particularly difficult when smoking animal protein because the rate of smoke absorption varies with the type and cut of animal protein.

With most smoking processes, the food product to be smoked is placed in an enclosed chamber called a smokehouse. The food product may be placed on racks or hangers within the smokehouse or pass through the smokehouse on a conveyor. The air in the smokehouse is charged with smoke from a smoke generator. The smoke generator may generate smoke by smoldering or burning wood, which may be selected from hickory, mesquite, cherry, beech wood, pecan wood, apple wood, and oak.

The smoke generator may be located outside the smokehouse, in which case the generated smoke is blown into the smokehouse through a duct. In other designs, the smoke generator may be integrated with the smokehouse. Most smokehouses also include an exhaust vent that may be powered and operate together with the smoke generator to regulate the smoke density in the air within the smokehouse. Smokehouses also may include a regulated heating system to maintain the temperature within the smokehouse within a desired range, and a humidifier to regulate humidity.

Factors including smoke density, temperature, food product residence time within the smokehouse, the type of food product being smoked, and the desired level of smoke absorption must be controlled to produce the desired level of smoke flavor in the food product. Typically, these factors are controlled by an experienced operator who relies on their skill at setting these operating parameters of the smokehouse. Such subjective setting and control can lead to inconsistent levels of smoke flavor absorbed by the food product between batches or runs, and between food product smokehouse facilities.

Attempts have been made to provide smokehouse operation that utilizes objective measurement techniques. In one example, sample smoke products are ground to make a slurry and their pH is measured to determine whether a desired level of smoke is absorbed by the smoked food product. Because smoke is acidic, an increase in the pH of a food product is indicative of an amount of smoke absorbed. A disadvantage with such a process is that it requires the continual destruction of the selected food product being smoked to monitor the progression of smoke absorption, and to determine when a desired amount of smoke absorption by the food product has occurred. This destructive testing creates food product waste that adds to the production cost of the smoking operation. Further, if the tested food product indicates that too much smoke has been absorbed by a batch or a run, the remaining food product of the run must be degraded as second-rate product or rejected as waste.

Accordingly, there is a need for a system and method for measuring smoke absorption into food products that does not require destructive testing of the food products, and that relies on objective measurements to promote consistency. There is also a need for a system and method for measuring smoke absorption into food products that operates and can be monitored in real time during the smoking operation, thereby optimizing the time required to achieve a desired amount of smoke absorption into the food product.

SUMMARY

The present disclosure describes systems and methods for measuring smoke absorption into a food product, and a method for making the system. The system and methods provide an objective determination of smoke absorption into a food product, thereby providing consistency and uniformity to the smoked food product produced without testing the food product itself. In exemplary embodiments, the disclosed system and method for measuring smoke absorption determine the amount of smoke absorbed into a food product in real time, which minimizes the likelihood of downgraded or rejected products due either to inadequate or excessive smoke absorption.

In an exemplary embodiment, a system for measuring smoke absorption into food products includes a surrogate that reacts to a presence of smoke in air ambient to the surrogate and to the food products and changes a state thereof to a preselected degree after an exposure to the smoke for a time sufficient to effect a predetermined amount of absorption of the smoke by the food products; and a probe in the form of a toroidal conductivity sensor that detects the change in the state of the surrogate, in embodiments a change in the electrical conductivity of the surrogate. In embodiments, exposure of the food products to the smoke in air ambient to the food products is terminated when a selected electrical conductivity of the surrogate is detected by the toroidal conductivity sensor.

In another exemplary embodiment, a system for measuring smoke absorption into food products includes a surrogate that reacts to a presence of smoke in air ambient to the surrogate and to the food products, the surrogate including an open container for containing a liquid and a toroidal conductivity sensor positioned in the open container that measures electrical conductivity of the liquid in the open container. The electrical conductivity of the liquid in the open container increases as the smoke in the air ambient to the surrogate is absorbed by the liquid in the open container and as the smoke in the air ambient to the surrogate is absorbed into the food products. A control that receives a signal from the toroidal conductivity sensor indicative of the electrical conductivity of the liquid and in response generates a signal and/or a display indicative of the electrical conductivity of the liquid in the open container that corresponds to a selected amount of smoke absorption by the food products exposed to the smoke in the air ambient to the surrogate. In embodiments, exposure of the food products to the smoke in air ambient to the food products is terminated when a selected electrical conductivity of the liquid is detected by the toroidal conductivity sensor.

In yet another exemplary embodiment, a method for measuring smoke absorption into food products includes exposing the food products to ambient air containing smoke and exposing a surrogate to the ambient air containing smoke. The surrogate includes a liquid in an open container that absorbs the smoke from air and changes electrical conductivity in response thereto. A toroidal conductivity sensor detects a predetermined degree of change in the electrical conductivity of the liquid after an exposure by the food products and the liquid to the ambient air containing smoke. In response to the toroidal conductivity sensor detecting the predetermined degree of change in the electrical conductivity of the liquid, a control ends the exposing of the food products to the ambient air containing smoke.

Other objects and advantages of the disclosed system and method for measuring smoke absorption into food products will be apparent from the following description, the accompanying drawings, and the appended claims.

DETAILED DESCRIPTION

Exemplary embodiments of a system for measuring the amount of smoke absorbed into a food product are described. As used herein, the terms "food product" and "food products" include any food or food ingredient for human consumption, and include meats, in particular pork bellies; fish; cheeses; sausages and other prepared meats; spices; vegetables, in particular root vegetables; fruits; nuts; and food ingredients. The disclosed systems utilize a surrogate, which is not itself the food product, nor is it derived from or taken from the food product that is smoked. Instead, the surrogate consists of or contains a substance that reacts to the chemical properties of smoke.

Smoke is mixture of different compounds dissolved or carried in air. It has been determined that acidic compounds make up approximately 96% of the smoke composition. Without being held to any particular theory, it is generally accepted that smoke is absorbed into a food product, such as a protein, by dissolving itself in water contained in the protein. As the protein cooks, the moisture is driven off, leaving the smoke compounds behind that are responsible for flavor and color changes to the food product.

Accordingly, in an exemplary embodiment described herein, the system utilizes a proxy or surrogate, such as water, in particular distilled or deionized water, as a suitable substitute or proxy to determine the amount of smoke absorbed into a food product, such as a moisture-laden protein, in particular a pork belly, while in a smokehouse. During the smoking process, the surrogate is tested to determine the rate of smoke absorption by the surrogate, which is indicative of the rate of smoke absorption into the food product.

In embodiments, the relation between the rate of smoke absorption into the surrogate and the rate of smoke absorption into the food product is determined empirically. A change of the state of the surrogate to a preselected degree caused by absorption of smoke into the surrogate, which may take the form of a change in pH of the water in the surrogate to a preselected degree, such as a preselected level of acidity, and/or a change in electrical conductivity of the water in the surrogate to a preselected degree, such as a preselected conductivity, is measured continuously during the smoking process. When the target pH and/or conductivity of the water in the surrogate is reached, the smoking process is completed for the food products in the smokehouse.

Figure 1:
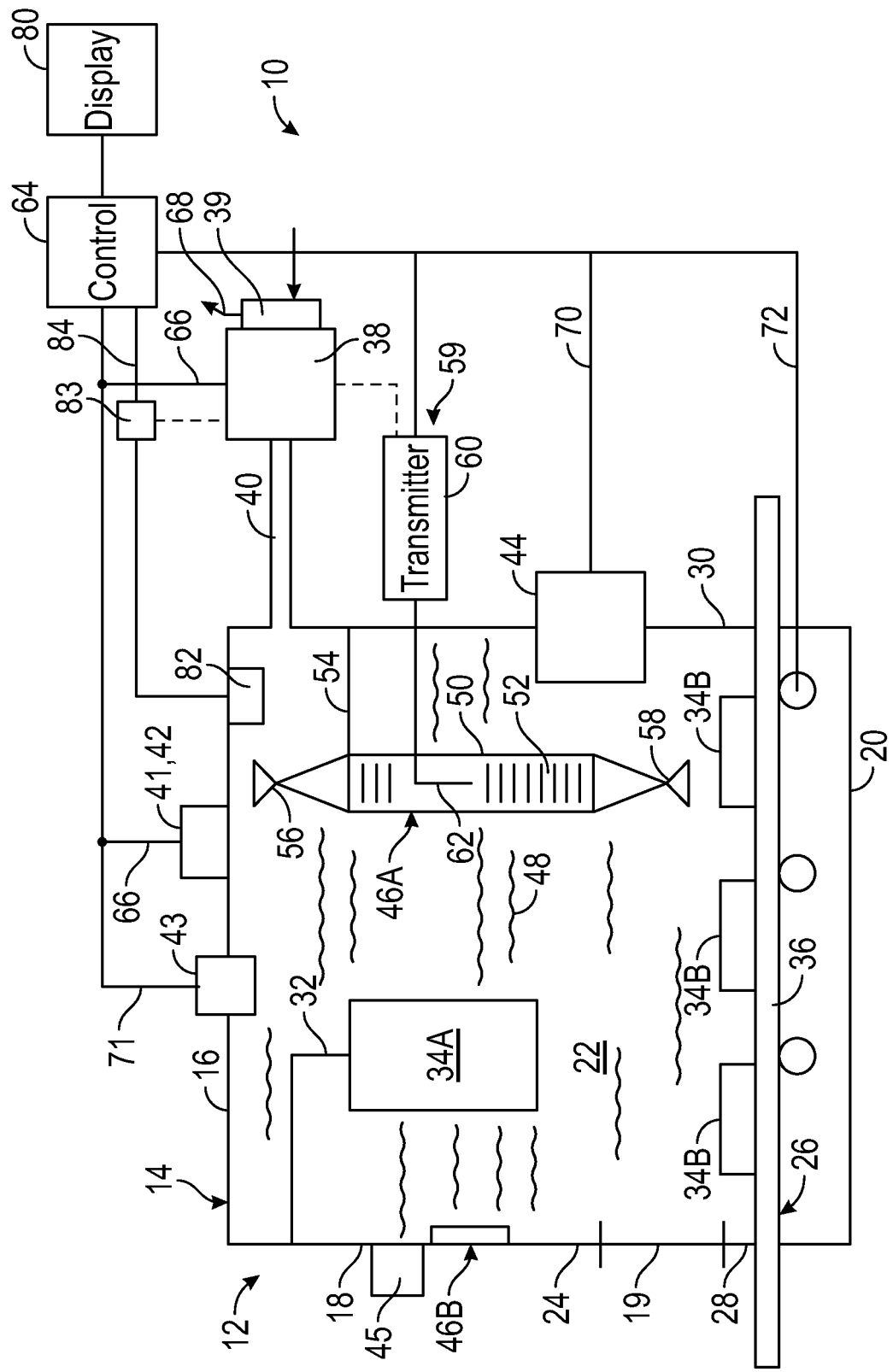
FIG. 1 is a schematic side elevation of a smokehouse incorporating an exemplary embodiment of the disclosed system for measuring smoke absorption into food products.

As shown in FIG. 1, an exemplary embodiment of the system for measuring smoke absorption into food products, generally designated 10, is used with, or incorporated into, a smokehouse, generally designated 12. The smokehouse 12 typically is an enclosed room 14 with a top wall 16, four side walls 18, and a floor 20 defining an interior 22 of the smokehouse. In an embodiment, one of the side walls 18, or an access door 19 in the wall, includes an inspection window 24 that allows an operator to view the interior 22. The access door 19 (there may be two or more, but only one is shown) enables an operator to enter to load and remove food products to be smoked. In an exemplary embodiment, the smokehouse 12 alternatively or in addition includes a conveyor 26 that passes through openings 28, 30 in opposing ones of the side walls 18.

As an alternative to the conveyor 26, or in addition to the conveyor, the smokehouse 12 in embodiments includes a rack system 32 for hanging food product 34A in the interior. The conveyor 26 includes a belt 36 that supports food product 34B and conveys it through the interior 22. The smokehouse 12 includes a smoke generator 38 that is connected to the interior 22 by a duct or conduit 40 and includes a smoke generator fan 39 for drawing ambient air into the smoke generator 38 and through the conduit to the interior of the smokehouse. In embodiments, the enclosed room 14 includes an intake vent 41 that in embodiments includes an intake fan, combined with an exhaust vent 42 that in embodiments includes an exhaust fan.

In embodiments, the smokehouse 12 may include a humidification valve 43 that allows steam and/or water mist into the interior 22 to regulate the humidity of the interior. The intake and exhaust vents 41, 42, respectively, are actuated in cooperation with the smoke generator 38 and smoke generator fan 39 to control the density of smoke in the interior 22. In exemplary embodiments, the smoke generator 38 generates smoke by burning or smoldering a selected combustible material, such as wood, for example hickory, mesquite, apple wood, oak, cherry, beech wood, pecan wood, and/or ash. The wood itself may be flavored with spices, essential oils, herbs, or spirits, such as bourbon.

The smoke generator fan 39 can be set to blow smoke into the interior 22 of the room 14 at selected flow rates, and the intake vent 41 and/or exhaust vent 42 can be adjusted to vary flow rates as well. The smokehouse 12 also may include a heater 44 for heating the interior. Both the fan powering the exhaust vent 42 and the heater 44 may be adjusted to vary the exhaust flow rate and the rate of heat input to the interior 22, respectively. The fan of the intake vent 41 is actuated to draw fresh air ambient to the exterior of the smokehouse, and the smoke generator fan 39 draws or blows smoke into the smokehouse 12. In embodiments, the smokehouse 12 also includes a thermometer and/or a thermostat, which may be incorporated into the heater 44, as well as a humidity sensor that may be incorporated into the humidification valve 43. In embodiments, the smokehouse 12 includes a circulation fan 45 that circulates the air containing smoke in the interior 22 of the enclosed room 14 of the smokehouse to provide even exposure of the food product 34A, 34B to the smoke 48.

The system 10 includes a proxy or surrogate 46A that reacts to a presence of smoke 48 in air ambient to the surrogate, namely, in the interior 22 of the smokehouse 12. The surrogate 46A changes state after an exposure to the smoke 48 for a time sufficient to effect a predetermined amount of smoke absorption by a selected food product 34A and/or 34B exposed to the smoke in the air ambient to the surrogate. The surrogate is not the food product 34A, 34B in the smokehouse 12, and is not derived from the food product in the smokehouse. In embodiments, the surrogate 46A is a liquid or a gel 52, and the change of state is a change in a state of the liquid or the gel. In an exemplary embodiment, the change in state is a change in electrical conductivity to a preselected degree of electrical conductivity of the liquid or gel 52. In another exemplary embodiment, the change in state of the surrogate 46A is a change in pH of the liquid or the gel 52 to a preselected pH value. In still other embodiments, the surrogate 46A includes a liquid 52 in the form of deionized or distilled water, and the change in state is a change in the electrical conductivity of the water.

In the embodiment shown in FIG. 1, the surrogate 46A is contained within a container 50 that takes the form of a casing made of a semi-permeable membrane that permits absorption of the smoke 48 from ambient air in the interior 22 of the smokehouse In embodiments, the semipermeable membrane casing 50 is made of material selected from animal intestine, cellulose, collagen, fibrous cellulose, and a polymer, all of which are permeable to smoke particles and gases, but impermeable to the liquid or the gel 52 contained in the semipermeable membrane of the casing, except through evaporation of the liquid as water vapor. In an exemplary embodiment, the casing 50 is cylindrical or tubular in shape and is tied or otherwise attached to and suspended downwardly from a bracket 54 that is mounted on one of the side walls 18 of the smokehouse 12.

In a particular embodiment, the surrogate 46A is contained within a 4-foot length of casing 50 that is tied off at its opposing ends 56, 58 and is suspended vertically within the interior 22. The casing 50 contains the liquid 52 that is retained in its interior. In an embodiment, the liquid 52 is water, and in particular deionized or distilled water. The system 10 also includes a sensor 59 that may take the form of a transmitter connected to a probe 62 to measure electrical conductivity or pH of the liquid 52 of the surrogate 46A. The probe 62 is mounted in the liquid 52 within the casing 50.

In embodiments, the probe 62 is connected by wire or wirelessly to communicate with the transmitter 60.

In an exemplary embodiment, the system 10 includes a control 64, which may take the form of a programmable logic controller (PLC) or a microcontroller. The control 64 is connected to receive a signal from the transmitter 60 indicative of the electrical conductivity or the pH of the liquid 52 of the surrogate 46A. The control 64 may receive a signal directly from the transmitter 60 wire or wirelessly. Alternatively, the probe 62 is wired directly to the control 64, which incorporates the transmitter. The control 64 is programmed to compare the electrical conductivity or pH measured by the probe 62 to a selected or desired target conductivity or pH for the selected food product 34A and/or 34B that corresponds to a selected degree of absorption of smoke 48 from the air ambient to the food product 34A, 34B. This selected or desired conductivity or pH is developed by conducting tests on various food products, in which a particular food product is tested using varied settings of smoke density, temperature, and residence time within the interior 22 of the smokehouse 12.

The control 64 is connected to the smoke generator 38, and intake vent 41 and exhaust vent 42 by cable 66, and smoke generator fan 39 by cable 68, heater 44 by cable 70, humidification valve 43 by cable 71, and conveyor 26 by cable 72. In embodiments, these communication and control connections are wired or wireless and/or part of a network, such as an Ethernet network or a controller area network (CAN). In an embodiment, the system 10 includes a smoke detector 82 connected to a transmitter 83 that is connected to the control 64 wirelessly or by a cable 84 and may be part of a network. The smoke detector 82 measures the density of the smoke 48 in the interior 22. In embodiments, the smoke detector 82 is mounted inside the enclosed room 14 of the smokehouse 12 to sample the density of the smoke 48 in the interior 22. An example of a suitable smoke detector 82 outputs a reading in parts per million of smoke in the air that is conveyed by the transmitter 83 to the control 64. The control 64 is programmed to actuate the smoke generator 38 and/or smoke generator fan 39 to maintain a selected smoke density in the interior 22.

In an exemplary embodiment, the control 64 is programmed to send an actuation signal to regulate the function of one or more of the smoke generator 38, the fan of intake vent 41 and fan of exhaust vent 42, which may act in tandem, the heater 44, the smoke generator fan 39, and the conveyor 26 in the smokehouse 12 containing the surrogate 46A and the food products 34A and/or 34B to obtain the measured conductivity or pH in a selected range after a selected time interval of residence in the smokehouse interior. In the case of the smoke generator 38, the control 64 can actuate the smoke generator fan 39 to increase or decrease the amount of smoke 48 generated and entering the interior 22 and vary the flow rate of the intake vent 41 and/or exhaust vent 42 fan. With the heater 44, the control 64 can increase or decrease the amount of heat generated and blown or radiated into the interior 22, and the control can increase or decrease the speed of the conveyor 26, thereby increasing or decreasing the residence time of the food products 34B in the interior 22 and consequent exposure to smoke 48.

Figure 2:
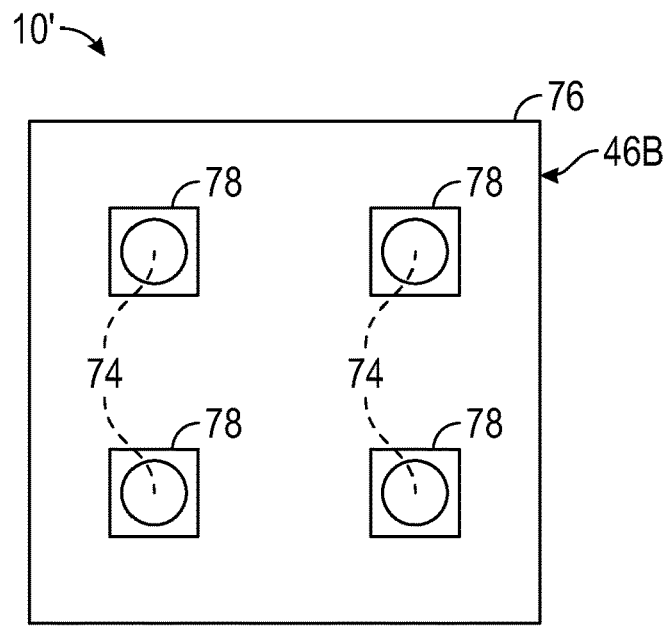
FIG. 2 is a schematic top plan view of another exemplary embodiment of the disclosed system for measuring smoke absorption into food products.

As shown in FIGS. 1 and 2, in another exemplary embodiment, the system 10' includes a proxy or surrogate 46B. The surrogate 46B is a disk 74, or multiple disks 74, of pH indicator applied to a substrate 76. The disks 74 may be in solid, liquid, or paste form. The disks 74 of pH indicator are covered by a smoke-permeable gel layer 78, which, in an exemplary embodiment is a whey protein gel layer. Also, in embodiments the pH indicator is phenolphthalein. The substrate 76 may be a polymer, such as nylon, glass, sized paper, cardstock, or a clear polymer, such as polyethylene terephthalate, an acrylic, or a polycarbonate.

The surrogate 46B is attached to the inside of the inspection window 24 of the smokehouse 12, by a releasable adhesive or suction cups (not shown) or hung from a hook or placed in the interior 22 where the disks 74 of pH indicators can be seen visually through the inspection window 24 by an operator. The thickness of the gel layer 78 is selected to permit penetration of the smoke 48 to the disks 74 at a selected rate that corresponds to a desired or a selected penetration rate of smoke into the food product 34A, 34B. The pH indicators of the disks 74 react when contacted with the acidic smoke that has penetrated the gel layer 78 and change color. The color change is a change in state of the surrogate 46B that indicates that a sufficient amount of smoke has absorbed into the food product 34A, 34B.

In another exemplary embodiment, shown in FIG. 1, the system 10 for measuring smoke absorption into food products 34A, 34B includes a surrogate 46A, which is not the food product, that absorbs smoke 48 in air within the smokehouse 12 ambient to the surrogate and to the food products and in response changes state. The surrogate 46A includes a casing 50 made of a semipermeable membrane. The casing 50 contains a liquid 52, which in embodiments is water, in particular distilled water and/or deionized water. Distilled and/or deionized water is not only pH neutral but has little or no electrical conductivity.

A sensor 59 in the form of an electrical conductivity meter having a transmitter 60 connected to a probe 62 that is positioned in the liquid 52 within the casing 50 to measure electrical conductivity of the liquid. The electrical conductivity of the liquid 52 in the casing 50 increases as the smoke 48 in the air ambient to the surrogate 46A penetrates the semipermeable membrane casing 50 and diffuses in the liquid 52, and as the smoke in the air ambient to the surrogate is absorbed into the food products 34A, 34B.

The control 64 generates a signal, which may take the form of an audible and/or visual alarm incorporated in the control, and/or a screen display on a display 80, indicating that a selected level of electrical conductivity of the liquid 52 has been reached that corresponds to a selected or desired amount of smoke absorption by the food products 34A, 34B exposed to the smoke 48 in the air ambient to the surrogate within the enclosed room 14 of the smokehouse 12. Alternatively, or in addition, the display 80 can receive a signal from the control 64 to show a real time pH and/or conductivity number readout and/or a graph showing cumulative absorption of smoke by the surrogate 46A. In embodiments, the control 64 includes a data store, which may be remote, to store all readings of the sensor, paired with a time stamp and stock keeping unit (SKU) of the food products, smoke density read by smoke detector 82, and other variables including smoke temperature, meat temperatures, wet bulb and dry bulb temperature, relative humidity, and food product residence time, for later reference.

The control 64 is adapted or programmed to regulate the function of one or more of the smoke generator 38 of the smokehouse 12 containing the surrogate 46A and the food products 34A, 34B, the intake vent 41 and exhaust vent 42, the humidification valve 43, the smoke generator fan 39, the conveyor 26, and the heater 44 and heater fan. In the embodiments disclosed herein, the food product 34A, 34B is selected from meats, in particular pork bellies, fish, cheeses, sausages and other prepared meats, spices, vegetables, in particular root vegetables, fruits, nuts, and food ingredients.

Figure 5:
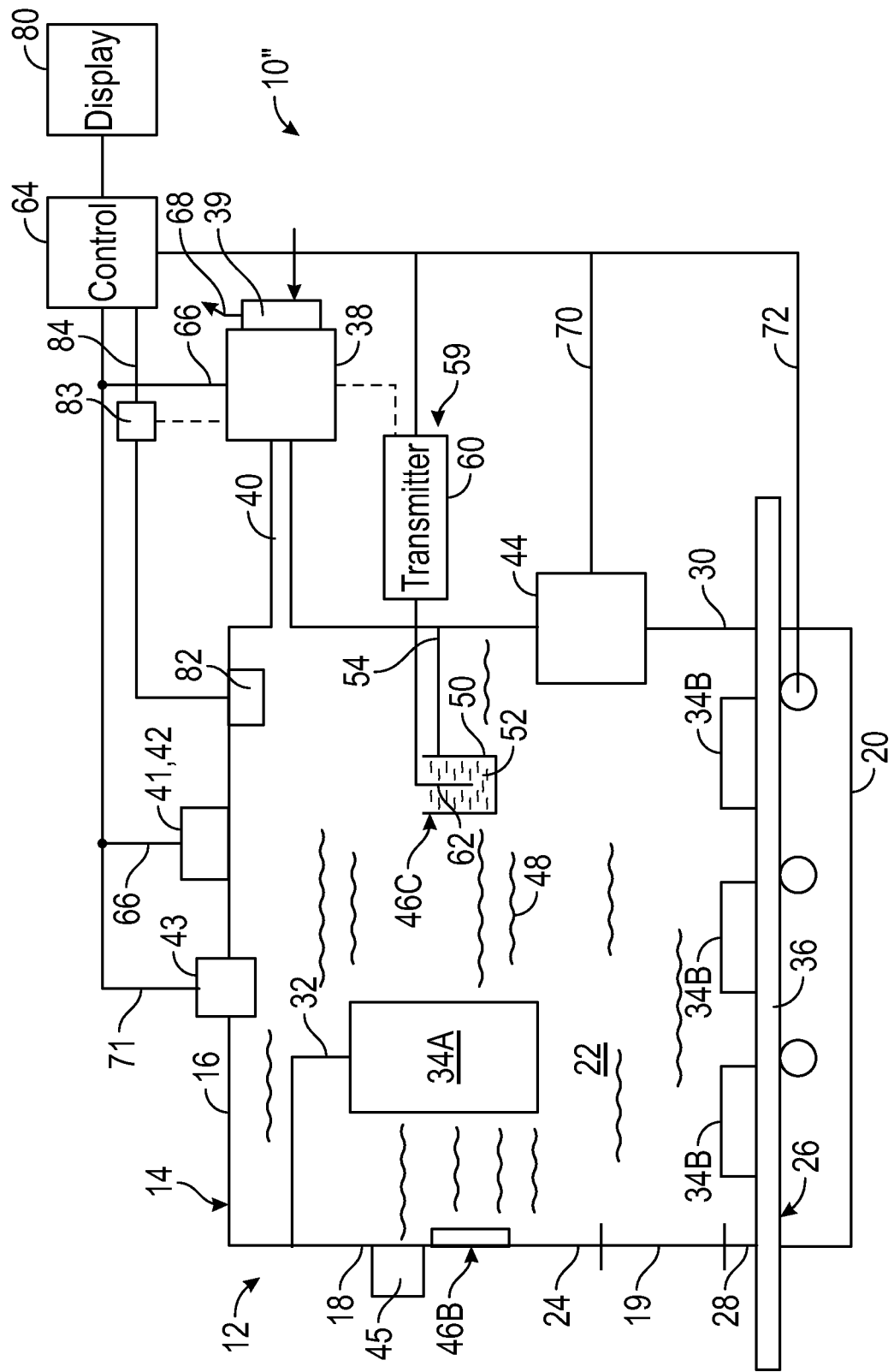
FIG. 5 is a schematic side elevation of a smokehouse incorporating another exemplary embodiment of the disclosed system for measuring smoke absorption into food products.

Another exemplary embodiment of the system, which is generally designated 10", is shown in FIG. 5. The system 10" for measuring smoke absorption into food products 34A and/or 34B includes a proxy or surrogate 46C, which is not the food product, that absorbs smoke 48 in air within the smokehouse 12 ambient to the surrogate and to the food products and in response changes state. The surrogate 46C is contained within a casing, which in this embodiment 10" takes the form of a container 50 having an open top. In embodiments, the container 50 is impermeable, such as a metal, glass, or plastic bucket or shallow pan. The container 50 contains a liquid 52, which in embodiments is water, in particular distilled water and/or deionized water. Distilled and/or deionized water is not only pH neutral but has little or no electrical conductivity.

In an exemplary embodiment, the container 50 is attached to, mounted on, or suspended downwardly from a bracket 54 that is mounted on one of the side walls 18 of the smokehouse 12. In other embodiments, the container 50 is attached directly to the smokehouse 12, such as to one of the side walls 18 thereof, or attached to suspended from the top wall 16, or placed on, supported by, or secured to the floor 20 of the enclosed room 14.

The sensor 59 takes the form of an electrical conductivity meter, or alternatively a pH meter, having a transmitter 60 connected to a probe 62 that is positioned in the liquid 52 within the container 50 to measure electrical conductivity of the liquid. The electrical conductivity of the liquid 52 in the container 50 increases as the smoke 48 in the air ambient to the surrogate 46C contacts the surface of the liquid at the open top of the container 50 and diffuses in the liquid, such as water, as the smoke in the air ambient to the surrogate is absorbed into the food products 34A, 34B.

The control 64 generates a signal, which may take the form of an audible and/or visual alarm incorporated in the control and/or a screen display on a display 80, indicating that a selected level of electrical conductivity, or selected pH, of the liquid 52 in the container 50 has been reached that corresponds to a selected or desired amount of smoke absorption by the food products 34A and/or 34B also exposed to the smoke 48 in the air ambient to the surrogate 46C within the enclosed room 14 of the smokehouse 12.

Alternatively, or in addition, the display 80 receives a signal from the control 64 to show a real time pH and/or conductivity number readout and/or a graph, or alternatively an indicator such as a color, indicative of cumulative absorption of smoke by the surrogate 46C. In embodiments, the control 64 includes a data store, which may be remote, to store all readings of the sensor 59, paired with a time stamp and SKU of the food products, smoke density read by smoke detector 82, and other variables including one or more of smoke temperature, meat temperatures, wet bulb and dry bulb temperature, relative humidity, and food product residence time, for later reference.

The control 64 is adapted to regulate the function of one or more of the smoke generator 38 of the smokehouse 12 containing the surrogate 46C and the food products 34A, 34B, the intake vent 41 and exhaust vent 42, the humidification valve 43, the smoke generator fan 39, the conveyor 26, the heater 44 and heater fan, and circulation fan 45. In the embodiments disclosed herein, the food product 34A, 34B is selected from meats, in particular pork bellies, fish, cheeses, sausages and other prepared meats, spices, vegetables, in particular root vegetables, fruits, nuts, and food ingredients.

Figure 3:
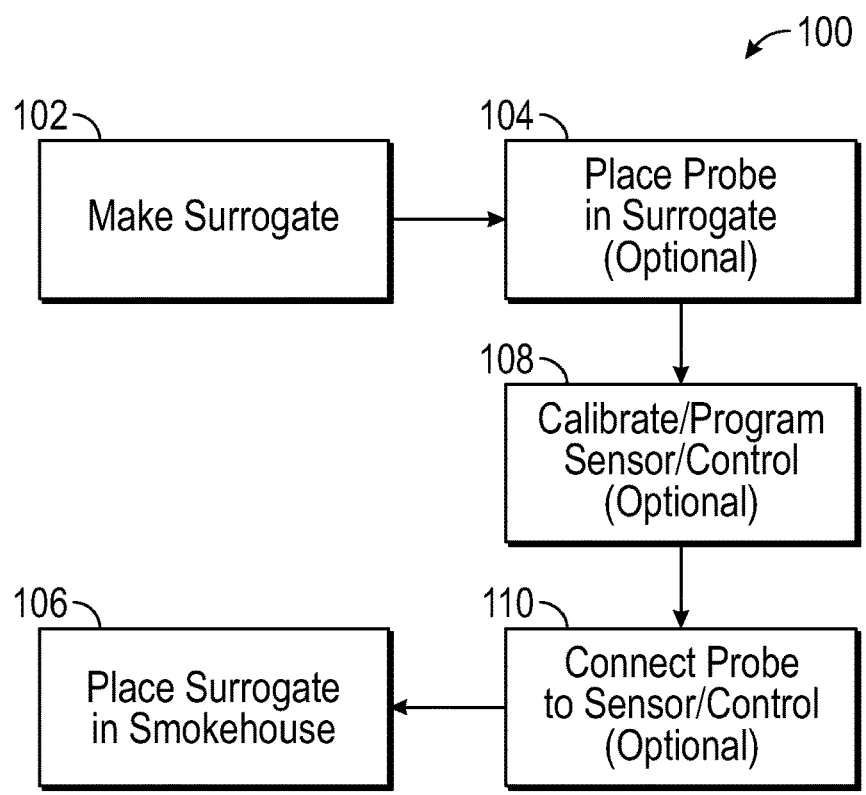
FIG. 3 is a flow chart showing an exemplary embodiment of a method for making the disclosed system for measuring smoke absorption into food products.

As shown in FIG. 3, a method 100 of making the system 10, 10', 10" for measuring smoke absorption into food products 34A, 34B begins with making the proxy or surrogate 46A, 46B, 46C as indicated by block 102. In the embodiment shown in FIG. 1, as indicated in block 104, making the surrogate 46A includes taking a casing 50 made of a semipermeable membrane, filling it with liquid or gel 52, placing a probe 62 in the liquid or gel within the casing, and in embodiments sealing the opposing ends 56, 58 of the casing to retain the liquid or gel and probe therein, as illustrated in FIG. 1 for system 10. In other embodiments, such as illustrated in FIG. 5 for system 10", the casing 50 is selected from an open container or pan 50 that may be plastic, glass, or metal. In embodiments, the liquid 52 is used and is water, in particular distilled water or deionized water.

In the embodiment shown in FIG. 2 for system 10', the surrogate 46B is made by attaching the disks 74, which may be of any shape in addition to round, of a pH indicator to a substrate 76, and covering the disks with the smoke-permeable gel layer 78. In the embodiment shown in FIG. 5 for system 10", the surrogate 46C is made by placing the container 50 in the interior 22 of the smokehouse 12, filling the container with liquid or gel 52, and placing the probe 62 in the liquid or gel.

As indicated in block 106, with embodiments of the systems 10, 10', 10" the surrogate 46A, 46B, 46C, respectively, is placed in the interior 22 of the smokehouse 12, where it will be exposed to smoke 48 in air ambient to the surrogate where the food products 34A, 34B are to be smoked. With each embodiment of the system 10, 10', 10" the surrogate 46A, 46B, 46C is configured to change its state after an exposure to the smoke 48 for a time sufficient to effect a predetermined amount of smoke absorption into the selected food product 34A, 34B exposed to the smoke in the air ambient to the surrogate.

As indicated in block 108, before or after placing the probe 62 of the sensor 59 in the surrogate 46A, 46C to measure a degree of the change of state of the surrogate, the sensor is calibrated or programmed to indicate a selected degree of the change of state of the surrogate corresponding to a selected amount of smoke 48 to be absorbed by the food products 34A, 34B. This calibration or programming utilizes data gathered empirically, recording smoke density, air temperatures, humidity, and residence time for various types and forms of food products 34A, 34B from previously conducted smokehouse 12 operations.

As indicated in block 110, if the system 10 is used, then the sensor 59 is connected to or incorporated in the control 64, and the control is configured to regulate the function of one or more of the smoke generator 38, the smoke generator fan 39, the intake vent 41 and exhaust vent 42, the humidification valve 43, the conveyor 26, the heater 44, and the circulation fan 45 of the smokehouse 12. With the system 10 of FIG. 1, as indicated in block 106, the surrogate 46A is placed in the smokehouse 12, which includes placing the casing 50 made of a semipermeable membrane in the smokehouse after the casing has been filled with the surrogate in the form of a liquid or gel 52, in embodiments water, and placing the probe 62 in the liquid. Placing the probe 62 of the sensor 59 in the surrogate 46A includes placing the probe in the surrogate to measure the electrical conductivity or the pH of the liquid 52. If necessary, the probe 62 is connected to the transmitter 60, which is connected to the control 64.

With the system 10" of FIG. 5, as indicated in block 106, the surrogate 46C is placed in the smokehouse 12, which includes placing the container 50 in the enclosed room 14 of the smokehouse and filling the container with the liquid 52, in embodiments distilled and/or deionized water, and placing the probe 62 in the liquid. Placing the probe 62 of the sensor 59 in the surrogate 46A, 46C includes placing the probe in the surrogate to measure the electrical conductivity and/or the pH of the liquid or gel 52 in the container 50.

Figure 4:
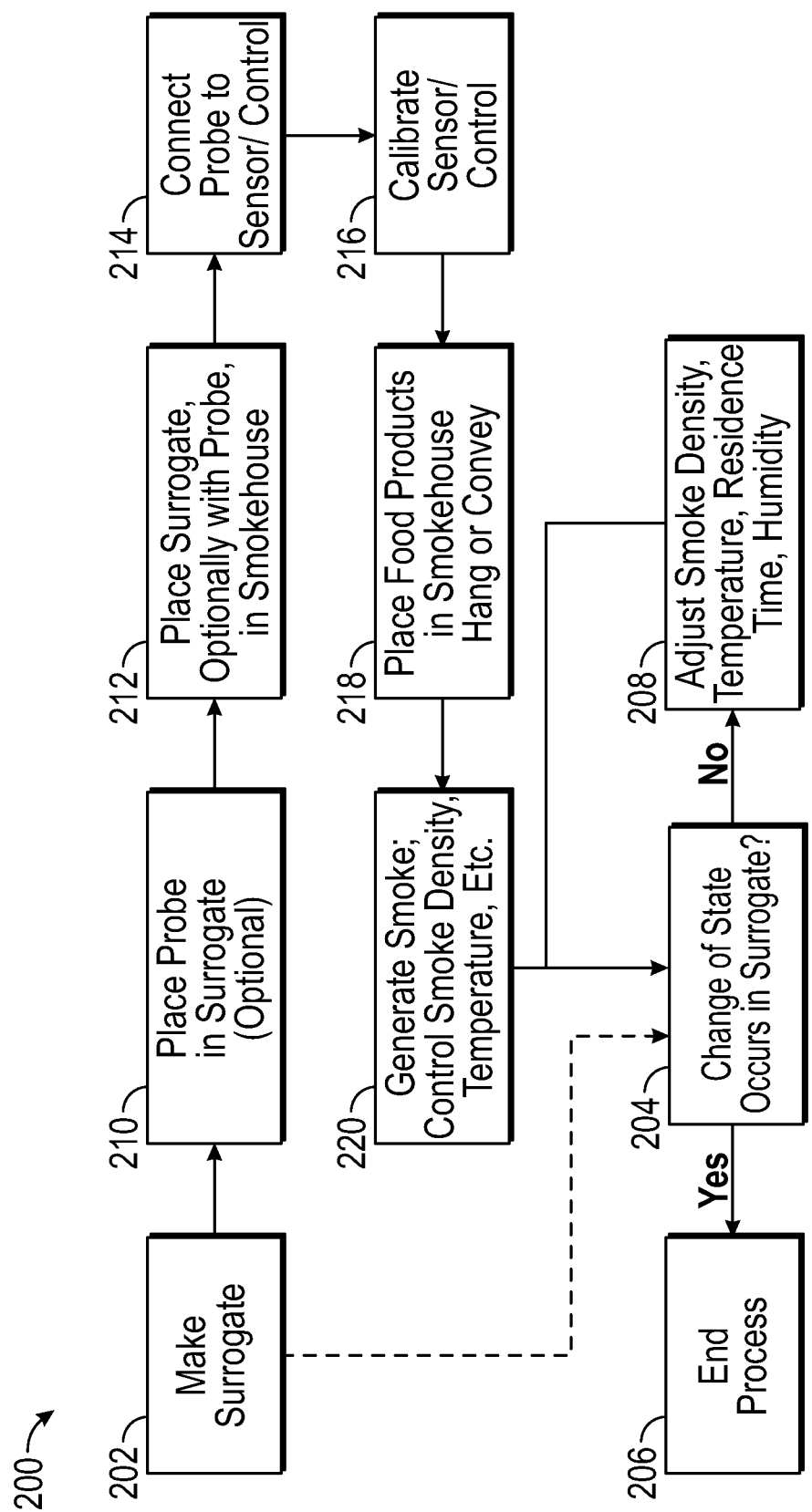
FIG. 4 is a flow chart showing an exemplary embodiment of a method for using the disclosed system for measuring smoke absorption into food products.

As shown in FIG. 4, a method for measuring smoke absorption into food products, generally designated 200, begins by placing the proxy or surrogate 46A, 46B, 46C that reacts to a presence of smoke 48 in air ambient to the surrogate in the presence of the food products 34A, 34B in the interior 22 of the enclosed room 14 of the smokehouse 12, as indicated in block 202. With the surrogate 46B of the system 10' of FIG. 2, the surrogate is mounted within the interior 22 where it can be observed visually through the inspection window 24. The next step is indicated by following dashed line from block 202 to block 204. The food products 34A, 34B are placed or conveyed into the interior 22 of the enclosed room 14 of the smokehouse 12, and the smoke generator 38 and smoke generator fan 39 actuated by the control 64 to create and convey smoke 48 into the interior to begin the smoking process. Temperature and humidity may be adjusted by the control 64 actuating the heater 44 and/or humidification valve 43.

As the smoke 48 penetrates the gel layer 78 to the disks 74 of the surrogate 46B, an operator detects a predetermined degree of change of the state of the disks 74 of the surrogate 46B after an exposure to the smoke 48 for a time sufficient to effect a predetermined or desired amount of smoke absorption into the food products 34A, 34B exposed to the smoke in the air ambient to the surrogate in the smokehouse 12. The change of the state of the disks 74 may take the form of a change in color of the disks.

As indicated in block 206, the process ends when the surrogate 46B changes state (i.e., changes color). Optionally, as indicated in block 208, during the process one or more of the food product residence time, smoke density, humidity, and/or air temperature are adjusted to accelerate the smoking process. After the process 200 is completed, the spent surrogate 46B is removed from the smokehouse 12 and replaced with a fresh surrogate 46B to begin the next process or batch. At this time the control 64 shuts off the smoke generator and heater 44, and actuates the intake and exhaust vents 41, 42 to remove the smoke 48 in the air ambient to the food products to end their smoke absorption.

With the embodiments of the systems 10 and 10" of FIGS. 1 and 5, respectively, as indicated in block 210, the probe 62 of sensor 59 is placed in the liquid or gel 52 of the surrogate 46A, 46C. Then, as indicated in block 212, the surrogate 46A 46C, with the probe 62, is placed in the smokehouse 12 with the food products 34A and/or 34B. The probe 62 is connected to the sensor 59, which may or may not be integral with the control 64, as indicated in block 214. Alternately, the surrogate 46A, 46C is first placed in the smokehouse 12, and the probe 62 of the sensor 59 is placed in the liquid or gel 62.

As indicated in block 216, the sensor 59 and/or control 64 is calibrated to a specific one or kind or type of the food product 34A, 34B (which may be specific to the type of food product, its thickness, and cut). In embodiments, the sensor 59 is calibrated and/or programmed, as is the control 64, to indicate a selected degree of the change of state corresponding to a selected amount of smoke 48 to be absorbed by the food products 34A and/or 34B. This calibration or programming utilizes data gathered empirically, recording smoke density, air temperatures, humidity, and residence time for various types and forms of food products 34B from previously conducted smokehouse 12 operations.

The calibration of block 216 may be performed at the beginning of the process, such as at the time of making the surrogate 46A, or the placement of surrogate in the smokehouse 12 and running tests for surrogate 46C. As indicated in block 218, the food products 34A, 34B are placed in the smokehouse 12, which includes either hanging the food products 34A on rack system 32 or placing them on the belt 36 of the conveyor 26 to be conveyed into the interior 22 of the smokehouse 12.

As indicated in block 220, the smoking process begins when the smoke generator 38 is actuated, which may be effected manually or automatically by the control 64 and includes actuation of the smoke generator fan 39. The control 64 monitors or detects the increase in the pH or the electrical conductivity of the liquid or gel 52 in the casing 50, which indicates a change of state of the surrogate 46A, 46C in real time during the food product smoking process, shown in block 204. as detected by sensor 59. If necessary, the control 64 adjusts the temperature by actuating the heater 44 and adjusts the density of the smoke 48 by actuating the smoke generator 38, the smoke generator fan 39, and/or the intake and exhaust vents 41, 42, respectively, and the humidity by actuating the humidification valve 43, as indicated in block 208.

As indicated in block 206, the process 200 ends when the desired pH or degree of electrical conductivity of the liquid or gel 52 is detected by the sensor 59, reading a signal from the probe 62 in the liquid or gel 52 of the surrogate 46A, 46C. The desired change of the state of the liquid or gel 52 in the casing or container 50 is transmitted to the control 64, which shuts down the smoke generator 38 and, optionally, actuates the intake and exhaust vents 41, 42, respectively, to clear the interior 22 of smoke 48, to end the smoking process. The food product 34A and/or 34B, having absorbed the desired amount of smoke 48, may then be removed from the smokehouse 12. If the conveyor 26 is used, the conveyor is indexed to the next array of food products 34B. The now-spent surrogate 46A, 46C (and in the case of the surrogate of FIG. 2, the spent surrogate 46B), is removed from the smokehouse 12 and replaced with a fresh surrogate in a similar manner.

At this time, if the system 10', 10" is operating in batch mode, the control 64 shuts off the smoke generator, smoke generator fan 39, and heater 44 and, optionally, actuates the intake and exhaust vents 41, 42 to remove the smoke 48 in the air ambient to the food products 34A and/or 34B in the enclosed room 14 of the smokehouse 12, to end their smoke absorption. If the system 10', 10" is operating in a continuous mode, the control 64 actuates the conveyor 26 to move the food products 34B on the conveyor out of the enclosed room 14 of the smokehouse 12 to end their smoke absorption.

Figure 6:
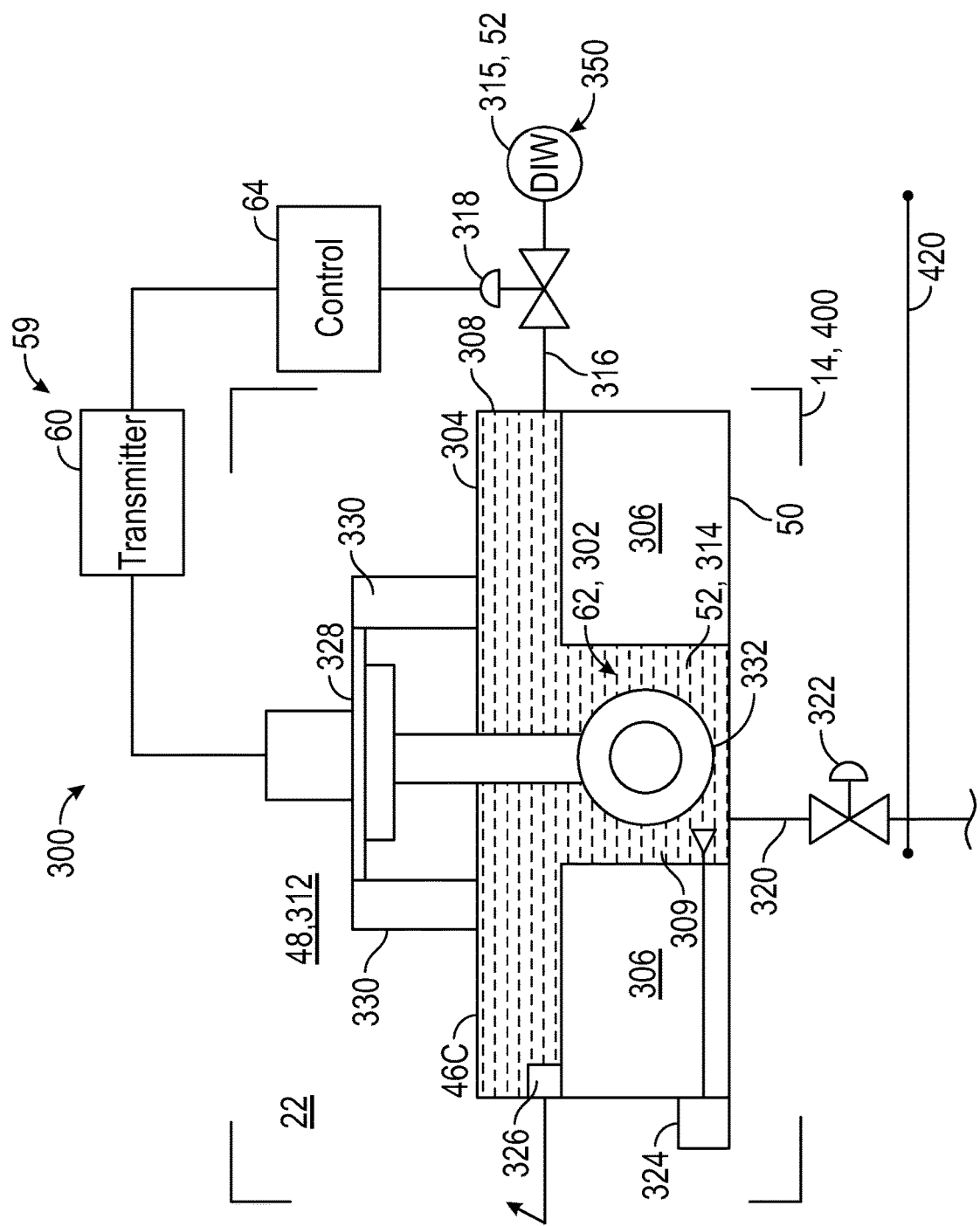
FIG. 6 is a schematic side elevation of an exemplary embodiment of a surrogate and probe of the embodiment of FIG. 5.

A system 300, which represents a specific embodiment of the system 10" of FIG. 5, is shown in FIG. 6. The system 300 includes a surrogate or proxy 46C that reacts to a presence of smoke 48 in air 312 ambient to the surrogate and changes a state thereof to a preselected degree after an exposure to the smoke for a time sufficient to effect a simultaneous predetermined amount of absorption of the smoke by a selected food product 34A and/or 34B (FIG. 5) exposed to the smoke in the air ambient to the surrogate. In this system 300, the surrogate or proxy 46C takes the form of the container 50 having an open top that holds a liquid 52 such a deionized and/or distilled water. The sensor 59 includes a probe 62 that takes the form of a toroidal conductivity sensor 302 that detects a change in the state of the liquid 52 of the surrogate 46C.

The open container 50 in embodiments is made of a plastic, such as polypropylene, having an open top 304, side walls 308 and an insert 306. In embodiments, the insert 306 is made of a plastic and defines a central well 309, which in embodiments is in the shape of a right cylinder. In embodiments, the well 309 is circular in horizontal cross section, and in other embodiments is elliptical, square, hexagonal, octagonal or otherwise polygonal, and free-form in shape. The well is shaped to receive the housing 332 containing the induction coils of the toroidal conductivity sensor 302. In embodiments, the insert 306 is attached to the interior of the container 50, such as by welding, by an adhesive, or is integrally molded with the container.

In embodiments, the toroidal conductivity sensor 302 includes a model EX2000RS sensor by Sensorex, Inc. of Garden Grove, Calif. In other embodiments, the toroidal conductivity sensor 302 includes a model ML-19504-00 toroidal conductivity transmitter connected to a model ML-30006-02 process meter (corresponding to the transmitter 60) by Cole-Parmer Instrument Company LLC of Vernon Hills, Ill. An advantage of utilizing such toroidal conductivity sensors 302 lies in their resistance to fouling and corrosion that might otherwise result from their use in the corrosive atmosphere of the smokehouse 12 and while remaining immersed in the liquid 52 of the surrogate 46C, which becomes increasingly acidic as the liquid absorbs smoke 48 during the smoking process.

In embodiments, the surrogate 46C includes a liquid 52 in which the change of state is a change in electrical conductivity of the liquid. In a particular embodiment, the change of state is a change in electrical conductivity of the liquid to a preselected degree of electrical conductivity. In the system 300, the toroidal conductivity sensor 302 is immersed in the liquid 52 in the open container 50. In an exemplary embodiment, the liquid 52 is deionized and/or distilled water 314 that is contained in the open container 50.

In embodiments, the toroidal conductivity sensor 302 is attached to a plate 328 that is connected to supports 330 that are attached to the side walls 308 of the container. In embodiments, the housing 332 containing the induction coils of toroidal conductivity sensor 302 functions as the probe 62 that sends, either by wire or wirelessly, a signal indicative of conductivity to a transmitter 60 of the sensor 59. In embodiments, the transmitter 60 sends a signal to the control 64 indicative of the electrical conductivity of the liquid 52. In some embodiments, the transmitter 60 is separate from the control; in other embodiments, the transmitter is incorporated in or is integral with the control 64.

In an embodiment, the surrogate 46C includes a circulation pump 324 mounted on the open container 50 to circulate the liquid 52 within the well 309 and a liquid sensor 326 for sensing the level of liquid 52 within the open container 50 to prevent underfilling or overfilling the open container. The circulation pump 324 is connected to the control 64 so that the control is capable of actuating the circulation pump to circulate the liquid 52 around the toroidal conductivity sensor 302 in the well 309 while conductivity measurements are taken. The liquid sensor 326 communicates with the control 64 so that the control actuates an inlet valve 318 to fill the open container to a predetermined level of liquid 52. In an embodiment, the insert 306 is sized such that an upper surface thereof lies below the surface of the liquid 314 in the container 50 to present a larger surface area to the air 312 ambient the system 300 and food products 34A, 34B than just the upper surface area of the right cylinder shape of the well 309.

In an embodiment, the surrogate 46C includes an inlet line 316 that conducts the liquid 52 into the open container 50 to fill the open container and immerse the housing 332 of the toroidal conductivity sensor 302. In an embodiment, the surrogate 46C includes a drain in the form of a drain line 320, in embodiments connected to the bottom of the open container 50, that drains the liquid 52 from the open container to empty the open container after use or as part of rinsing the container. In an embodiment, the inlet line includes the inlet valve 318 and the drain line 320 includes a drain valve 322, both actuated by the control 64, so that the control effects the filling and draining of the container 50.

In embodiments, in the system 300 the control 64 is connected to receive a signal from the transmitter 60 and toroidal conductivity sensor 302 of sensor 59 indicative of the electrical conductivity of the liquid 52 in the open container 50. The control 64 is programmed to compare the electrical conductivity of the liquid 52, which in embodiments is deionized and/or distilled water 314, in the open container 50 to a selected conductivity for the selected food product. In embodiments, the selected conductivity values are stored in the control 64 and correspond to the types of food product 34A and/or 34B to be smoked, and/or is received by the control 64 from a remote source (not shown) such as a personal computer, either by wire or wirelessly and/or over a network.

In embodiments, the control 64 is programmed to send an actuation signal to regulate a function of one or more of the smoke generator 38, the fan in the intake vent 41, the smoke generator fan 39, the circulation fan 45, the fan in the exhaust vent 42, the heater 44, and the conveyor 26, all associated with the smokehouse 12 containing the surrogate 46C and the food products 34A and/or 34B, to obtain a measured conductivity in a selected range after a selected time interval. In embodiments, the control 64 is programmed to actuate the inlet valve 318 to fill the open container 50 with the liquid 52 and to actuate the drain valve 322 to drain the liquid 52 from the open container 50.

The system 300 for measuring smoke absorption into food products 34B thus includes a surrogate 46C that reacts to a presence of smoke 48 in air 312 ambient to the surrogate and to the food products. In an embodiment, the surrogate 46C includes an open container 50 for containing the liquid 52. A toroidal conductivity sensor 302 is positioned in the open container 50 and measures the electrical conductivity of the liquid 52 in the open container. The electrical conductivity of the liquid 52 in the open container 50 increases as the smoke 48 in the air 312 ambient to the surrogate 46 C is absorbed by the liquid in the open container and as the smoke in the air ambient to the surrogate is absorbed into the food products. The control 64 receives a signal from the toroidal conductivity sensor 59 and in response generates a signal and/or a display 80 indicative of the electrical conductivity of the liquid 52 in the open container 50 that corresponds to a selected amount of smoke absorption by the food products 34B exposed to the smoke 48 in the air 312 ambient to the surrogate 46C.

The control 64 is programmed to actuate one or more of the inlet valve 318 to fill the open container 50 with the liquid 52, the drain valve 322 to drain the liquid from the open container after the selected amount of smoke absorption by the food products 34B, and the circulation pump 324 to recirculate the liquid 52 in the open container while the probe 62 in the form of the toroidal conductivity sensor 302 of sensor 59 measures the electrical conductivity of the liquid in the open container. The control 64 is adapted to regulate the function of one or more of the smoke generator 38 of the smokehouse 12 containing the surrogate 46C and the food products 34A and/or 34B, the fan in the intake vent 41 that draws smoke into the smokehouse, the smoke generator fan 39 that draws air ambient the smokehouse through the smoke generator 38, the circulation fan 45 that circulates smoke-laden air 312 ambient to the food products and surrogate within the enclosed room 14 of the smokehouse, the exhaust vent 42, the food products conveyor 26, and the heater 44.

In embodiments, the open container 50 is connected to a source 315 of liquid 52, such as deionized water 314, by the inlet line 316. The source 315 in embodiments may take the form of a holding tank, which may be pressurized. The inlet valve 318, which in embodiments is a control valve, on the inlet line is connected to the control 64 so that the control actuates the inlet valve to cause liquid 52 from the source 314 to enter and fill the open container 50. The drain valve 322, which in embodiments is a control valve, is actuated by the control 64 to selectively drain the liquid 52 from and empty the open container.

Figure 7:
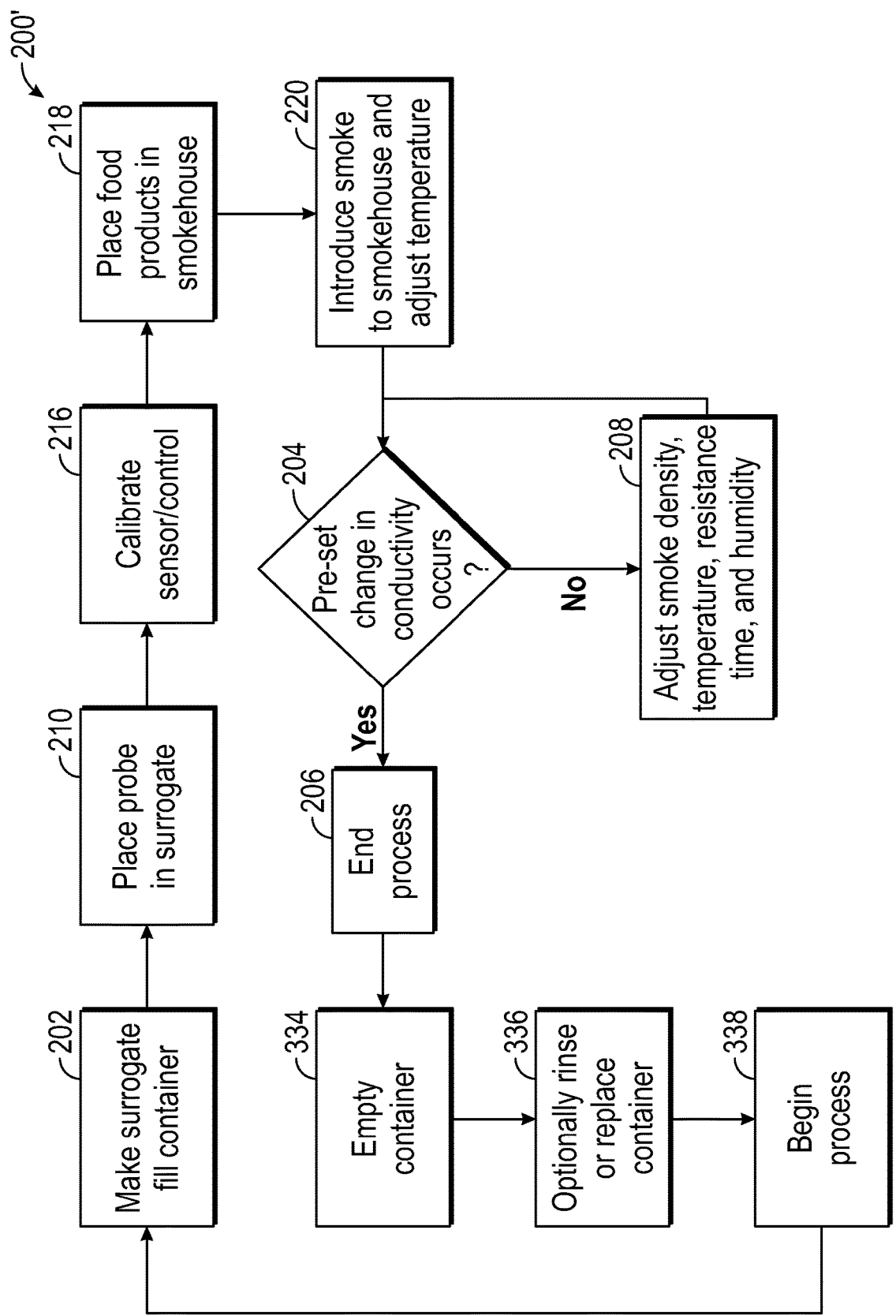
FIG. 7 is an embodiment of the flow chart of FIG. 4 of a method for using the disclosed system with the surrogate and probe of FIG. 6.

In operation, the system 300 of FIGS. 5 and 6 in embodiments follows the process 200' shown schematically in FIG. 7. In general, the process 200' includes exposing the food products 34B to ambient air 312 containing smoke 48 and simultaneously exposing the surrogate 46C to the ambient air 312 containing smoke 48. In an embodiment, the surrogate 46C includes a liquid 52 in an open container 50 that absorbs smoke 48 from the ambient air 312 and changes electrical conductivity in response thereto. The process continues with detecting a predetermined degree of change in the electrical conductivity of the liquid 52 by a toroidal conductivity sensor 302 after an exposure by the food products 34B and the liquid 52 to the ambient air 312 containing smoke 48. In response to detecting the predetermined degree of change in the electrical conductivity of the liquid 52, the process ends by ending the exposing of the food products 34A and/or 34B to the ambient air 312 containing smoke 48, at which time the food products have absorbed a selected amount of smoke 48 from the ambient air 312.

In embodiments, ending the exposing of the food products 34A and/or 34B to the ambient air 312 containing smoke 48 includes one or both of removing the food products from the ambient air containing smoke and removing the ambient air containing smoke from contacting the food products, for example by exhausting the ambient air containing smoke through the exhaust vent 42 from the enclosed room 14. In embodiments, detecting a predetermined degree of change in the electrical conductivity of the liquid 52 by a toroidal conductivity sensor 59 includes circulating the liquid in the open container in contact with the toroidal conductivity sensor by the circulation pump 324.

In embodiments, the process continues with replacing the liquid 52 in the open container 50 after the ending the exposing of the food products 34B to the ambient air 312 containing smoke 48. In embodiments, the process includes regulating a function of one or more of a smoke generator 38 of a smokehouse 12 containing the food products 34B for generating the ambient air 312 containing smoke 48, the fan in the intake vent 41 that draws the ambient air into the smokehouse, the circulation fan 45 that circulates the ambient air 312 containing smoke 48 within the smokehouse, the smoke generator fan 39 that draws air ambient the smokehouse 12 into the smoke generator 38, the exhaust vent 42 of the smokehouse, the food products conveyor 26, and the heater 44. In an exemplary embodiment, exposing the surrogate 46C to the ambient air 312 containing smoke 48 includes a surrogate with deionized water and/or distilled water 314 as the liquid 52.

In a particular embodiment, the process 200' for utilizing the system 300 shown schematically in FIG. 7 begins by making the surrogate 46C, which is indicated in block 202 as filling the open container 50 with the liquid 52. In an embodiment, the control 64 actuates the inlet valve 318 to an open configuration to convey deionized water 314 from the source 315 through inlet line 316 to the open container 50. The fill level of deionized and/or distilled water 52 in the open container 50 is monitored by the control 64 utilizing sensor 326. As indicated in block 210, the probe 62 in the form of the toroidal conductivity sensor probe 302 is placed in the well 309 of the surrogate 46C, as the open container 50 fills with deionized water 314. As indicated in block 216, the toroidal conductivity sensor 59 at this time is optionally calibrated by the control 64, which measures any conductivity of the deionized water 314 as a baseline.

However, at the end of the process for the system 300, indicated in block 206 in FIG. 7, the control 64 actuates the drain valve 322 (FIG. 6) to open and drain the liquid 52, which in embodiments is deionized and/or distilled water 314, that has absorbed smoke from the open container 50, as indicated in block 334. In embodiments, also at this time the control 64 actuates the intake vent 41 and the exhaust vent 42 to exhaust the smoke 48 from the interior 22 of the smokehouse 12 (FIG. 5). In the embodiment of the smokehouse 12 of FIG. 5, the conveyor 26 is then indexed to move the smoked food product 34B from the smokehouse 12 through opening 30 and unsmoked food product into the smokehouse through opening 28. Smoked food product 34A may be removed manually.

At this time, in embodiments, the control 64 actuates the drain valve 322 to a closed position and opens the inlet valve 318 to refill the open container 50 with liquid 52 to a predetermined level as indicated by liquid sensor 326. Optionally, the control closes the inlet valve 318 and opens the drain valve 322 to rinse out the open container 50 by emptying the open container of liquid 52 before beginning a subsequent smoking process, as indicated in block 336. In embodiments, this rinse step of block 336 is repeated multiple times between smoking operations.

Alternatively, in another embodiment, the system 300 includes a container 50 that is disconnected from inlet line 316 and drain line 320 and the toroidal conductivity sensor 59 is removed after one use. The container 50 is then replaced with a fresh container that is connected to inlet and drain lines 316, 320, respectively, and receives the probe 302 of the toroidal conductivity sensor 59. The process begins, as indicated in block 338 and proceeds as indicated in block 202 where the fresh container 50 is then filled with fresh, unused liquid 52 from inlet line 316 to make the surrogate 46C. Once the open container 50 is refilled with fresh liquid 52, the surrogate 46C is recharged or remade, as indicated in block 202 in FIGS. 4 and 7, and ready for a subsequent smoking process 200. In still another embodiment, the filling, rinsing, and emptying the liquid 52 from the open container 50 is performed manually without using inlet and drain lines 316, 320, respectively.

Another exemplary embodiment of the disclosed method for measuring smoke absorption into food products 34B begins by exposing the food products to ambient air 312 containing smoke 48 and exposing a surrogate 46C to the ambient air containing smoke. The surrogate 46C includes a liquid 52 in an open container 50 that absorbs the smoke 48 from the ambient air 312 and changes electrical conductivity in response thereto. The method continues with detecting a predetermined degree of change in the electrical conductivity of the liquid 52 by the toroidal conductivity sensor 59 after an exposure by the food products 34B and the liquid 52 to the ambient air 312 containing the smoke 48. In response to detecting the predetermined degree of change in the electrical conductivity of the liquid 52, the process ends exposing the food products 34B to the ambient air 312 containing smoke 48.

In an embodiment, ending exposing the food products 34B to the ambient air 312 containing smoke 48 includes one or both of removing the food products from the ambient air containing smoke, as by transporting them on the conveyor 26 from the smokehouse 12, and/or removing the ambient air containing smoke from contacting the food products, as by exhausting the ambient air containing smoke from the smokehouse 12 through the exhaust vent 42 and shutting off the smoke generator 38 and smoke generator fan 39. In an embodiment, detecting a predetermined degree of change in the electrical conductivity of the liquid 52 by the toroidal conductivity sensor 302 includes circulating the liquid in the open container 50 in contact with the toroidal conductivity sensor, as by the circulation pump 324.

In an embodiment, the liquid 52 in the open container 50 is replaced after the ending the exposure of the food products 34B to the ambient air 312 containing smoke 48. In an embodiment, the method includes regulating the function of one or more of the smoke generator 38, the smoke generator fan 39, the fan in the intake vent 41, the circulation fan 45, the exhaust vent 42, the food products conveyor 26, and the heater 44. In embodiments, this regulating or modulating is effected by the control 64, which may implement a stored program and/or rely on, or modify the stored program based on, feedback on electrical conductivity from the toroidal conductivity sensor 59. In a particular embodiment, the method is performed in which exposing the surrogate 46C to the ambient air 312 containing smoke 48 includes using a surrogate having deionized and/or distilled water 314 as the liquid 52.

Figure 8:
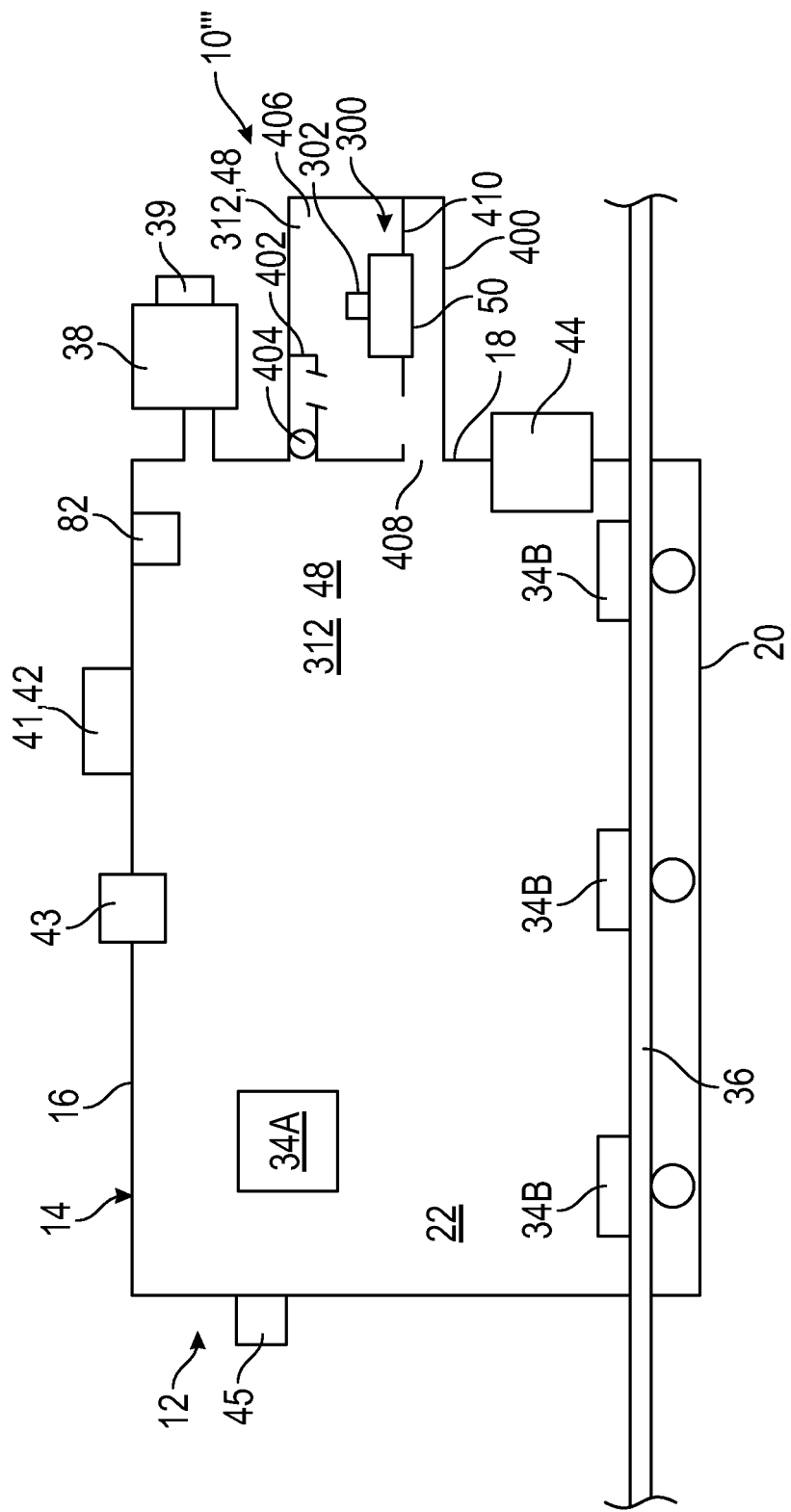
FIG. 8 is a schematic side elevation of a smokehouse incorporating yet another exemplary embodiment of the disclosed system for measuring smoke absorption into food products.

As shown in FIGS. 6 and 8, in another embodiment of the system, generally designated 10''', the system 300 is contained within a housing 400 that is physically separate from the enclosed room 14 of the smokehouse 12. The enclosed housing 400 includes an inlet duct 402 that communicates with the interior 22 of the enclosed room 14 and in embodiments incudes an inlet fan 404. The inlet fan 404 in embodiments is connected to and is actuated by the control 64 to draw air 312 ambient the food products 34A and/or 34B into the interior of the housing 400, where it contacts the liquid 52 in the container 50 of the surrogate 46C. In an embodiment, the housing includes an outlet duct 408 that communicates with the interior 22 of the enclosed room 14 so that air 312 ambient the food products 34A and/or 34B circulates from the interior of the enclosed room through the interior of the housing 400 containing the surrogate 46C.

In embodiments, the container 50 is supported within the housing by a panel 410. In other embodiments, the container 50 rests upon the floor or lower surface of the interior of the housing 400. In various embodiments, the housing 400 is mounted on one of the side walls 18 of the smokehouse 12, the top wall 16 of the smokehouse, and on the floor adjacent the smokehouse 12. In embodiments where the housing 400 is physically separate from the smokehouse 12, the inlet duct 402 and outlet duct 408 take the form of flexible hoses that interconnect the interior 22 of the enclosed room 14 with the interior of the housing 400. With such embodiments, the inlet fan 404 would be mounted in the inlet duct 402 or in the housing 400 adjacent the duct.

With other such embodiments the housing 400 is mounted on a movable support 420 (FIG. 6), which may take the form of a wheeled cart, dolly, or a self-propelled vehicle. With such embodiments, the housing 400 can be connected to and disconnected from multiple smokehouses 12 serially to perform the smoking process, such as shown schematically in FIG. 7. With such embodiments, the control 64 is mounted or carried on the housing 400, or optionally on the movable support 420. Alternatively, the system 300 connects, either by wire or wirelessly, to a control or controls 64 that is/are connected to and actuate the components of multiple smokehouses 12.

With the system 10''' of FIGS. 6 and 8, the method of operation of the system 300 is the same as for the system 10'' of FIG. 5. The food products 34A and/or 34B are placed or conveyed into the enclosed room 14 of the smokehouse 12. The control 64 actuates the smoke generator 38 and smoke generator fan 39 to introduce the ambient air 312 containing smoke 48 into the interior 22 of the enclosed room 14 of the smokehouse. The control 64 actuates the inlet fan 404 to draw the ambient air 312 containing smoke 48 through the inlet duct 402 into the interior of the housing 400. There, the container 50 of surrogate 46C, which has been charged with deionized and/or distilled water 314 from the holding tank 350 so that the toroidal conductivity sensor 302 is submerged within the well 309, is exposed to the ambient air 312 containing smoke 48, which increases the electrical conductivity of the deionized and/or distilled water 314 in the container 50.

The probe 62 int the form of the toroidal conductivity sensor 302 of the sensor 59 detects this change in electrical conductivity and the transmitter 60 transmits a signal indicative of this change to the control 64. When the predetermined level of electrical conductivity of the deionized and/or distilled water 314 is reached and detected by the control 64, indicating a predetermined amount of absorption of smoke 48 by the food products 34A and/or 34B, the control advances the conveyor 26 to remove the food products 34B from the smokehouse 12 and/or the food products 34A are removed from the smokehouse. Optionally, the control 64 stops the smoke generator 38 and smoke generator fan 39. The control 64 actuates the drain valve 322 to drain the liquid 52 from the container 50, optionally fills the container and drains it to rinse the container and probe 302, and the fills the container with deionized water and/or distilled water 314 to begin a new smoking process.

The foregoing systems and methods provide objective, repeatable means for measuring smoke absorption into a wide array of food products. Moreover, the methods and systems are employed in real time, during the smoking process, which minimizes the possibility of oversmoking or undersmoking the food products. This may result in a reduction in the amount of time a food product needs to remain in the smokehouse, and a reduction in the amount of smoke needed to produce the desired color and flavor changes in the food product. Moreover, use of the disclosed systems and methods over time would enable operators to determine the exact levels of desired smoking for many types of food products, and reducing waste due to quality downgrades. While the forms of apparatus and methods described herein are preferred embodiments of the disclosed system and process for measuring smoke absorption into food products, and method of making, it should be understood that the invention is not limited to these specific systems and processes, and that changes may be made therein without departing from the scope of the invention.

What is claimed is:

1. A system for measuring absorption of smoke into food products, the system comprising:
    a surrogate located in an interior of a smokehouse containing the food products, the surrogate including an open container containing a liquid or a gel layer that reacts to a presence of the smoke in air ambient to the surrogate and the food products and changes a state thereof to a preselected degree after an exposure to the smoke for a time sufficient to effect a predetermined amount of absorption of the smoke by the food products exposed to the smoke;
    wherein the liquid or the gel is selected from deionized water and/or distilled water and the gel layer is selected from polyethylene terephthalate, an acrylic, and a polycarbonate; and
    the surrogate includes a circulation pump mounted to circulate the liquid or the gel layer within the open container; and
    the surrogate includes a probe including a toroidal conductivity sensor that detects the change of state of the surrogate, wherein the toroidal conductivity sensor is immersed in the liquid or the gel layer in the container.

2. The system of claim 1, wherein the the change of state is a change in electrical conductivity or pH of the liquid or the gel layer.

3. The system of claim 1, wherein the surrogate includes an inlet line that conducts the liquid or the gel into the open container to fill the open container and immerse the toroidal conductivity sensor.

4. The system of claim 1, wherein the surrogate includes a drain that drains the liquid from the open container.

5. The system of claim 1, further comprising a control that is connected to receive a signal from the toroidal conductivity sensor indicative of the electrical conductivity or the pH of the liquid or the gel layer in the open container.

6. The system of claim 5, wherein the control is programmed to compare the electrical conductivity of the liquid or the gel layer in the open container to a selected conductivity of the liquid for the food products.

7. The system of claim 6, wherein the control is programmed to send an actuation signal to regulate a function of one or more of a smoke generator, a smoke generator fan, an intake fan, a circulation fan, an exhaust vent, a heater, and a conveyor in a smokehouse containing the surrogate and the food products to obtain a measured conductivity by the probe in a selected range after a selected time interval.

8. The system of claim 6, wherein the control is programmed to actuate an inlet valve to fill the open container with the liquid and/or actuate a drain valve to drain the liquid from the open container.

9. The system of claim 1, wherein the surrogate is located in an interior of a smokehouse containing the food products.

10. The system of claim 1, further comprising a housing containing the surrogate, the housing being exterior of a smokehouse containing the food products and communicating with an interior of the smokehouse to receive the air ambient to the food products in the interior of the smokehouse such that the air ambient to the food products contacts the surrogate in the housing.

11. A system for measuring absorption of smoke into food products, the system comprising:

a surrogate that reacts to a presence of the smoke in air ambient to the surrogate and to the food products, the surrogate including an open container containing a liquid or a gel;

a probe including a toroidal conductivity sensor positioned in the open container that measures electrical conductivity or pH of the liquid or the gel layer in the open container;

wherein the electrical conductivity or the pH of the liquid in the open container increases as the smoke in the air is absorbed by the liquid in the open container and as the smoke in the air is absorbed into the food products; and a control that receives a signal from the toroidal conductivity sensor indicative of the electrical conductivity or the pH of the liquid or the gel layer in the open container and in response generates a signal and/or a display indicative of the electrical conductivity of the liquid or the gel layer in the open container that corresponds to a selected amount of smoke absorption by the food products exposed to the smoke in the air ambient to the surrogate.

12. The system of claim 11, wherein the control is programmed to actuate one or more of an inlet valve to fill the open container with the liquid, a drain valve to drain the liquid from the open container after the selected amount of smoke absorption by the food products, and a circulation pump to circulate the liquid in the open container while the toroidal conductivity sensor measures the electrical conductivity of the liquid in the open container.

13. The system of claim 11, wherein the control is adapted to regulate a function of one or more of a smoke generator for a smokehouse containing the food products, an intake fan that draws smoke into the smokehouse, a circulation fan that circulates smoke-laden air within the smokehouse, an exhaust vent of the smokehouse, a food products conveyor in the smokehouse, and a heater that heats the air ambient to the surrogate in the smokehouse.

14. A method for measuring absorption of smoke into food products, the method comprising:

placing the food products into an interior of a smokehouse;

blowing or drawing smoke into the interior of the smokehouse;

exposing the food products to ambient air in the interior containing the smoke;

exposing a surrogate that is not the food products and is not derived from the food products to air ambient to the surrogate that reacts to a presence of smoke in air ambient to the surrogate in the interior, wherein the surrogate changes state after an exposure to the smoke for a time sufficient to effect a predetermined amount of smoke absorption by the food products exposed to the smoke, the exposing including an open container containing a liquid or a gel layer, the liquid selected from distilled or deionized water that changes electrical conductivity or pH in response thereto;

detecting a predetermined degree of change in the electrical conductivity or the pH of the liquid by a toroidal conductivity sensor after the exposure by the food products and the liquid to the ambient air containing the smoke; and in response to detecting the predetermined degree of change in the electrical conductivity or the pH of the liquid by the toroidal conductivity sensor, ending exposing the food products to the ambient air containing the smoke.

15. The method of claim 14, wherein ending the exposing of the food products to the ambient air containing the smoke includes one or both of removing the food products from the ambient air containing the smoke and removing the ambient air containing the smoke from contacting the food products.

16. The method of claim 14, wherein detecting the predetermined degree of change in the electrical conductivity of the liquid by the toroidal conductivity sensor includes circulating the liquid in the open container in contact with the toroidal conductivity sensor.

17. The method of claim 14, further comprising replacing the liquid in the open container after ending exposing food products to the ambient air containing the smoke.

18. The method of claim 14, further comprising regulating a function of one or more of a smoke generator for generating the ambient air containing the smoke in a smokehouse containing the food products, an intake fan that draws the ambient air containing the smoke into the smokehouse, a circulation fan that circulates the ambient air containing the smoke in the smokehouse, an exhaust vent of the smokehouse, a food products conveyor in the smokehouse, and a heater that heats the ambient air containing the smoke in the smokehouse.

19. The method of claim 14, wherein exposing the surrogate to the ambient air containing the smoke includes exposing the surrogate including deionized water or distilled water as the liquid to the ambient air containing the smoke.

20. The method of claim 14, wherein ending exposing the food products to the ambient air containing smoke includes removing the ambient air containing smoke from contacting the food products by one or more of regulating by a control a function of one or more of a smoke generator, an intake fan, a recirculation fan, an exhaust vent, a food products conveyor into the interior of the smokehouse, and a heater by a control.

21. The method of claim 14, wherein placing the food products into an interior of a smokehouse; blowing or drawing smoke into the interior of the smokehouse; exposing the food products to ambient air in the interior containing the smoke; exposing the surrogate to the ambient air containing the smoke, the surrogate including an open container containing the liquid or a gel layer selected from distilled or deionized water in an open container that changes the electrical conductivity or the pH in response thereto; detecting the a predetermined degree of change in the electrical conductivity or the pH of the liquid by a toroidal conductivity sensor after an exposure by the food products and the liquid to the ambient air containing the smoke; and ending exposing of the food products to the ambient air containing smoke are performed in real time during a smoking process.

22. The method of claim 21, wherein the pH indicator is phenolphthalein and the gel layer is a polymer selected from nylon, glass, sized paper, cardstock, a clear polymer such as polyethylene terephthalate, an acrylic, and a polycarbonate.

23. The method of claim 14, further comprising initially conveying the food products through the interior of the smokehouse on a conveyor.

24. The method of claim 23, further comprising blowing or drawing smoke into the interior of the smokehouse through a conduit by a smoke generator.

* * * * *

UNITED STATES PATENT AND TRADEMARK OFFICE
CERTIFICATE OF CORRECTION

| | | |
|---|---|---|
| PATENT NO. | : 11,561,213 B2 | |
| APPLICATION NO. | : 17/089287 | |
| DATED | : January 24, 2023 | |
| INVENTOR(S) | : Robert E. Hanson and Richard L. McKenzie | |

It is certified that error appears in the above-identified patent and that said Letters Patent is hereby corrected as shown below:

In the Claims

Column 18, Line 28 Claim 2 reads:
"...claim 1, wherein the the..."

Should read:
--...claim 1, wherein the...--

Signed and Sealed this
Twenty-eighth Day of February, 2023

Katherine Kelly Vidal
*Director of the United States Patent and Trademark Office*